United States Patent
Zhou et al.

(10) Patent No.: US 11,911,477 B2
(45) Date of Patent: Feb. 27, 2024

(54) USE OF FRUCTOSE IN PREPARING DRUG FOR TREATING ISCHEMIC INJURY

(71) Applicant: Beihang University, Beijing (CN)

(72) Inventors: Bing Zhou, Beijing (CN); Xunming Ji, Beijing (CN); Jing Liang, Beijing (CN); Panpan Yu, Beijing (CN); Rongrong Han, Beijing (CN)

(73) Assignee: Beihang University, Beijing (CN)

( * ) Notice: Subject to any disclaimer, the term of this patent is extended or adjusted under 35 U.S.C. 154(b) by 0 days.

(21) Appl. No.: 17/646,935

(22) Filed: Jan. 4, 2022

(65) Prior Publication Data
US 2022/0211853 A1 Jul. 7, 2022

(30) Foreign Application Priority Data
Jan. 4, 2021 (CN) .......................... 202110001626.4

(51) Int. Cl.
*A61K 47/36* (2006.01)
*A61P 25/00* (2006.01)
*A61K 45/06* (2006.01)

(52) U.S. Cl.
CPC .............. *A61K 47/36* (2013.01); *A61K 45/06* (2013.01); *A61P 25/00* (2018.01)

(58) Field of Classification Search
CPC ......... A61K 47/36; A61K 31/70; A61P 25/00; A61P 25/28
See application file for complete search history.

(56) References Cited

U.S. PATENT DOCUMENTS 5,128,354 A * 7/1992 Masuda ............... C07D 261/20
514/379

OTHER PUBLICATIONS

Yusuke Yamamoto, et al., "Pentose phosphate pathway activation via HSP27 phosphorylation by ATM kinase: A putative endogenous antioxidant defense mechanism during cerebral ischemia-reperfusion," Brain Research 1687 (2018), p. 82-94; available online Mar. 3, 2018.
Song Xiaoping, "Glycerol Fructose Injection Makes Patients with Coronary Heart Disease Feel More at Ease and Comfortable," Medical Economic News No. 012 Issuance, Jun. 29, 2009.
Fan Dagong, et al. "Comparative Study of the Effects of Glycerol Fructose Injection and Mannitol on Ischemic Infarction," Journal of Giqihar Medical College, 2002, vol. 23, No. 7, p. 754, received Apr. 24, 2002.

* cited by examiner

*Primary Examiner* — Robert T. Crow
*Assistant Examiner* — John P Nguyen
(74) *Attorney, Agent, or Firm* — Workman Nydegger

(57) ABSTRACT

The present disclosure provides use of fructose in preparing a drug for treating a cerebral ischemic stroke, and relates to the technical field of biomedicine. In the present disclosure, an ischemic injury cell model and an ischemic injury animal model are established, and fructose treatment is conducted on the injury models; and it is found that the fructose can regulate energy metabolism and redox metabolism of neurons, and reduce an ischemic injury of model cells and model animals. Specifically, the present disclosure includes: reducing a neuronal mortality after the ischemic injury, reducing an area of cerebral infarction in animals with the ischemic injury, and improving neurobehavioral characteristics of the animals.

18 Claims, 20 Drawing Sheets

USE OF FRUCTOSE IN PREPARING DRUG FOR TREATING ISCHEMIC INJURY

CROSS REFERENCE TO RELATED APPLICATION(S)

This patent application claims the benefit and priority of Chinese Patent Application No. 202110001626.4, filed on Jan. 4, 2021, the disclosure of which is incorporated by reference herein in its entirety as part of the present application.

TECHNICAL FIELD

The present disclosure relates to the technical field of biomedicine, in particular to use of fructose in preparing a drug for treating an ischemic cerebral injury.

BACKGROUND ART

Cerebral stroke, as one of the most important diseases causing death and disability, brings a severe burden on the society and families. There are about 80% of cerebral stroke patients suffering from cerebral ischemic stroke. In the past few years, a great progress was made in diagnosis and treatment of the cerebral ischemic stroke, and most patients can be treated with drugs or surgeries. But relying on thrombolysis and thrombectomy within a time window, only about 46% of patients have a desirable prognosis (90 d of modified rankin scale (mRS) with 0-2 points), and there are still risks such as symptomatic intracranial hemorrhage (SICH), such that the comprehensive treatment effect is far lower than expected. Therefore, there is an urgent need for more effective and safe strategies for prevention and treatment of the cerebral ischemic stroke.

When cerebral ischemic stroke occurs, there are symptoms such as local arterial occlusion, decreased cerebral blood flow (CBF), deep hypoxia of brain tissue and microvascular dysfunction, triggering an imbalance of metabolic homeostasis. The blood supply, oxygen supply and carbohydrate supply of brain tissue are reduced or completely stopped, and redox metabolism is unbalanced, such that a large number of oxygen free radicals are produced. Moreover, when the CBF is lower than 10 ml/(100 g min), the energy of penumbra is exhausted, causing irreversible necrosis on cells to further evolve into an infarct core. Therefore, when ischemia occurs, it is essential to alleviate the ischemic injury and promote a desirable functional outcome by maintaining a steady state of redox and energy metabolism. This is also an important drug treatment target for the cerebral ischemic stroke.

In the prior art, there is a glycerol fructose injection as a highly-osmotic dehydrating drug. The glycerol can participate in to improve cerebral metabolism; the fructose can be metabolized without insulin; and the sodium chloride can regulate electrolyte balance. The product has a mechanism of action as follows: after intravenous injection, the product can increase plasma osmotic pressure, causing water in tissues (including eyes, brain and cerebrospinal fluid) to enter blood vessels, thereby reducing tissue edema, reducing intracranial pressure, intraocular pressure and cerebrospinal fluid volume and pressure; meanwhile, the water contained in the tissues is promoted to move to blood to dilute the blood, thereby reducing edema around capillaries and improving microcirculation, such that a cerebral perfusion pressure is increased, and a cerebral blood flow is increased. The product is a first-line drug for clinically reducing intracranial pressure and eliminating cerebral edema.

There is fructose-1,6-bisphosphate in the prior art. The fructose diphosphate sodium is an important product of cell metabolism, and can regulate activities of several enzymes in carbohydrate metabolism. Exogenous fructose diphosphate sodium can act on cell membrane to increase concentrations of high-energy phosphate bonds and adenosine triphosphate (ATP) in the cell membrane by activating fructokinase on the cell membrane. Therefore, the fructose diphosphate sodium can promote influx of potassium ions to restore a resting state of cells, increase a content of adenosine diphosphate (ADP) in red blood cells, and inhibit releases of oxygen free radicals and histamine. Accordingly, the fructose diphosphate sodium can be used as a molecular-level drug for restoring and improving cell metabolism, to clinically assist the treatment of coronary heart disease, arrhythmia, acute cerebral infarction and other diseases.

The common metabolic pathways of carbohydrates in the body include glycolytic pathway and pentose phosphate pathway. The glycolytic pathway, also known as an Embden-Meyerhof-Parnas (EMP) pathway and as a common glucose degradation pathway in all biological organisms, is a series of reactions that degrade glucose and glycogen into pyruvate (accompanied by generation of ATP). The glycolytic pathway, capable of being conducted under anaerobic and aerobic conditions, is a common metabolic pathway for aerobic or anaerobic decomposition of glucose. The pentose phosphate pathway is a way of oxidative decomposition of glucose. Since starting with glucose-6-phosphate (G-6-P), this pathway is also called a hexose phosphate shunt pathway. This pathway is conducted in cytoplasm and can be divided into two stages. The first stage starts from dehydrogenation of the G-6-P to produce 6-phosphoric acid, then to produce 6-phosphoric acid by hydrolysis, and then to produce 5-phosphoric acid by oxidative decarboxylation. Nicotinamide adenine dinucleotide phosphate (NADP+) is an electron acceptor in all the above oxidation reactions. The second stage is that 5-ribulose phosphate undergoes a series of ketonic group and aldehyde group transformation reactions, and finally produces 3-phosphoglyceraldehyde and fructose-6-phosphate through intermediate metabolites such as tetrose phosphate, pentose phosphate and heptose phosphate. The 3-phosphoglyceraldehyde and the fructose-6-phosphate can also re-enter the glycolytic pathway for metabolism.

Compare to the fructose-1,6-bisphosphate in the prior art., the derivates of Fructose includes F-1-P, F-1,6-P, F-6-P and uric acid, which can further modulate the intracellular oxidative status based on their high antioxidative capacity. These circulating derivates were also shown to be more efficient in OH scavenging and iron sequestration, which is one of the key mechanisms of neuronal stress in disease.

However, there are few studies on fructose pathways in the current technology especially in the nerve system and stroke or brain edema. Further exploration is needed regarding the regulation of neuronal redox and energy metabolism by the fructose pathways, and there is no application record of treatment cerebral ischemic stroke through the fructose pathways. The present disclosure reports for the first time that the fructose can regulate a metabolic network to treat ischemic cerebral injury.

SUMMARY

An objective of the present disclosure is to provide use of fructose in preparing a drug for treating an ischemic cerebral injury. The fructose regulates energy metabolism and redox metabolism of neuronal cells to improve the ischemic cerebral injury.

To achieve the above objective, the present disclosure provides the following technical solutions.

The present disclosure provides use of fructose in preparing a pharmaceutical composition for treating an ischemic cerebral injury. The fructose improves an ischemic injury, such as the ischemic cerebral injury, by regulating neuronal energy metabolism and redox metabolism.

In the present disclosure, the fructose can be used in different routes of administration, including but not limited to intravenous administration, intramuscular injection, local administration, intraperitoneal injection, intracranial injection, intrathoracic administration, intracranial administration, transpulmonary administration, subcutaneous administration, sublingual administration, oral administration, nasal drip administration, interventional administration, implantable drug administration, application, transdermal administration, smearing administration and intrarectal administration. Further, a blood-brain barrier effect may be reduced in the form of the intravenous injection and the intracranial administration, which is beneficial to improve an efficiency of drugs.

In the present disclosure, the fructose can be administered during an acute cerebral infarction stage, a stroke rehabilitation stage, and stages before and after thrombolysis and stages before and after thrombectomy.

In the present disclosure, the fructose has different pharmaceutical dosage forms, including but not limited to an injection, a powder injection, a drop, a patch, a tablet, a granule, a sublingual tablet, a microinjection, an effervescent tablet, a solution, an emulsion, a liposome preparation, a suspension, an ointment, a cream, a transdermal absorption, a transmucosal absorption, a lozenge, a drop, a drop pill, a pill, a capsule, a powder, a pulvis, a liniment, a fine granule and a syrup.

Further, the pharmaceutical composition of the present disclosure may include the fructose or a pharmacologically acceptable salt thereof as an effective ingredient; meanwhile, the following agents may be optionally added as needed in preparation of drugs: an excipient, a binder, a disintegrant, a lubricant, a diluent, a solubilizer, a suspending agent, an isotonic agent, a pH regulator, a buffer, a stabilizer, a coloring agent, a flavoring agent and a corrigent.

In the present disclosure, the pharmaceutical composition can be modulated, shaped or prepared according to methods commonly used in the field. Further, the pharmaceutical composition may be prepared into a state that is easy to store by freeze-drying, and dissolved in diluents such as water, physiological saline and buffer to obtain an appropriate concentration during use.

In the present disclosure, the fructose in the pharmaceutical composition may have a concentration of 0.1-15 mM, preferably 0.5-10 mM, more preferably 1-8 mM, and furthermore preferably 1-6 mM.

In the present disclosure, the ischemic injury includes an ischemic cerebral injury, a cerebral ischemic stroke, and ischemia and a hypoxic injury of other organs or parts, such as a myocardial ischemic injury and a kidney ischemic injury.

In the present disclosure, the pharmaceutical composition can be used alone, or optionally used with other active ingredients. The pharmaceutical composition can be administered at the same time or at intervals, and the interval administration can be within a time range when each active ingredient acts simultaneously; a route of administration and a method of administration can be the same or different; the pharmaceutical composition can be prepared separately or stored in a single package suitable for combination medication. In the present disclosure, an ischemic injury protection drug is developed based on the fructose or direct metabolic pathway products of the fructose, such as fructose-1-phosphate (F-1-P) and fructose-1,6-diphosphate (F-1, 6-P), Fructose-6-P(F-6-P) and uric acid, The beneficial effects are as follows: in the present disclosure, by using a middle cerebral artery occlusion (MCAO) injury model and a neuron oxygen-glucose deprivation (OGD) injury model for a rat, it is observed for the first time that the fructose pathway is important in regulating neuronal energy metabolism and redox metabolism, and a metabolism map is drawn for the fructose pathway. It is found that the fructose pathway can inhibit the ischemic injury to neurons and inhibit the behavioral changes caused by the ischemic injury, which has a protective effect on the ischemic cerebral injury. In addition, in the present disclosure, the fructose is selected as the active ingredient to conduct a regulatory effect on the redox and energy metabolisms of neurons in ischemic cerebral injury. The fructose can significantly increase a viability of the neurons, improve an activity and a survival rate of damaged neurons, improve neurobehavior and reduce an area of cerebral infarction. Therefore, the fructose shows outstanding therapeutic effects on the ischemic cerebral injury, with a stronger effect than other similar drugs in the prior art.

DETAILED DESCRIPTION OF THE EMBODIMENTS

To better explain the objectives, technical solutions, and advantages of the present disclosure, the present disclosure will be further explained below with reference to accompanying drawings and specific examples. The described embodiments are merely some rather than all of the embodiments of the present disclosure. All other embodiments obtained by a person of ordinary skill in the art on the basis of the embodiments of the present invention without creative efforts shall fall within the protection scope of the present invention.

Example 1 Selection of a Fructose Pathway 1.1. Establishment of a Cerebral Ischemic Stroke Model (1) Cell model: the cerebral ischemic stroke was simulated using an OGD model, DIV7 primary neurons were treated with a glucose-free medium in a hypoxic box (1% $O_2$+5% $CO_2$+94% $N_2$), oxygen glucose deprivation was conducted at 37° C. for 1.5 h, and the primary neurons was cultured in a normal medium for 24 h under normoxic conditions.

(2) Animal model: the cerebral ischemic stroke was simulated using an MCAO-injured model in the rats, 250-300 g of male Sprague-Dawley (SD) rats were anesthetized with isopentane, and fixed on an operating table supinely. The neck skin was cut off, subcutaneous tissues and muscles were bluntly separated to expose the common carotid artery, internal carotid artery and external carotid artery, the common carotid artery was clipped with an arterial clip, and a ligature was threaded on each of the internal carotid artery and the external carotid artery. The external carotid artery was cut off to form an open, a suture plug was introduced and pushed gently to a beginning of the middle cerebral artery to form MCAO, fixation was conducted by a suture, the suture plug was removed 1.5 h after operation, and blood flow reperfusion was conducted; the rats were returned to the cage for 24 h of feeding, and neurobehavioral evaluation is conducted; after anesthesia, the rats were sacrificed, and brains were taken for triphenyltetrazolium chloride (TTC) staining to observe an area of cerebral infarction.

1.2. Metabolic Disorders Caused by the Cerebral Ischemic Stroke

Figure 1A:
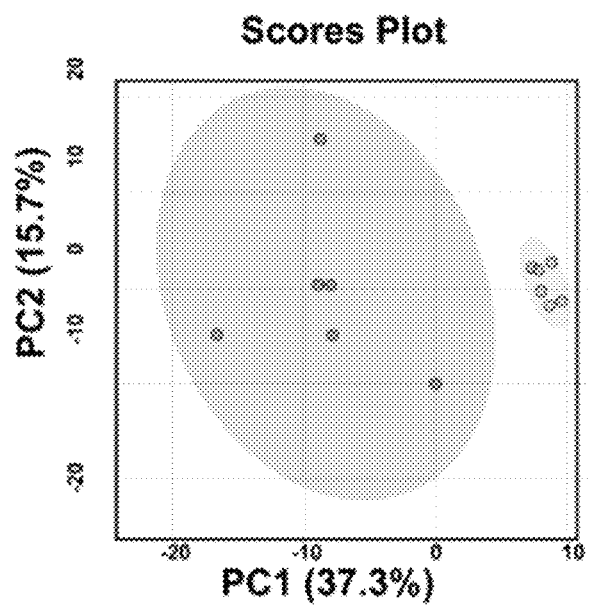
FIGS. 1A-D shows metabolome changes in a cerebral cortex of a cerebral stroke model rat.
Figure 1B:
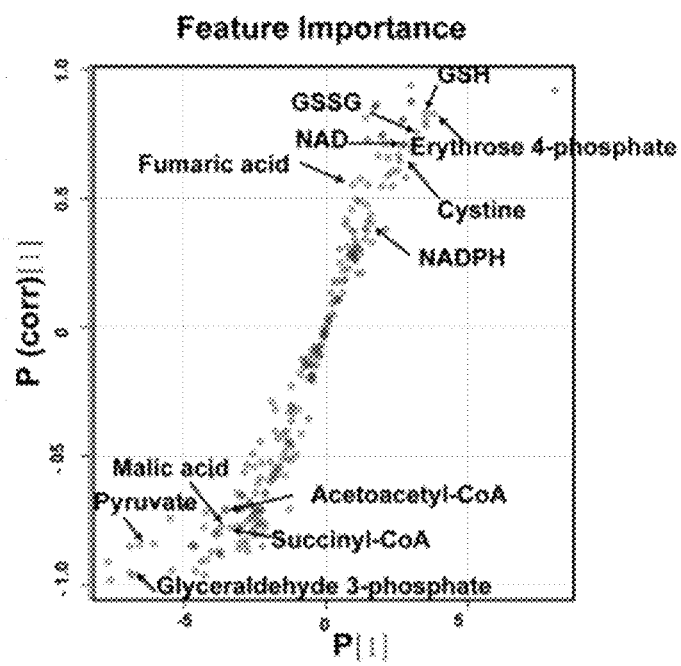
Figure 1C:
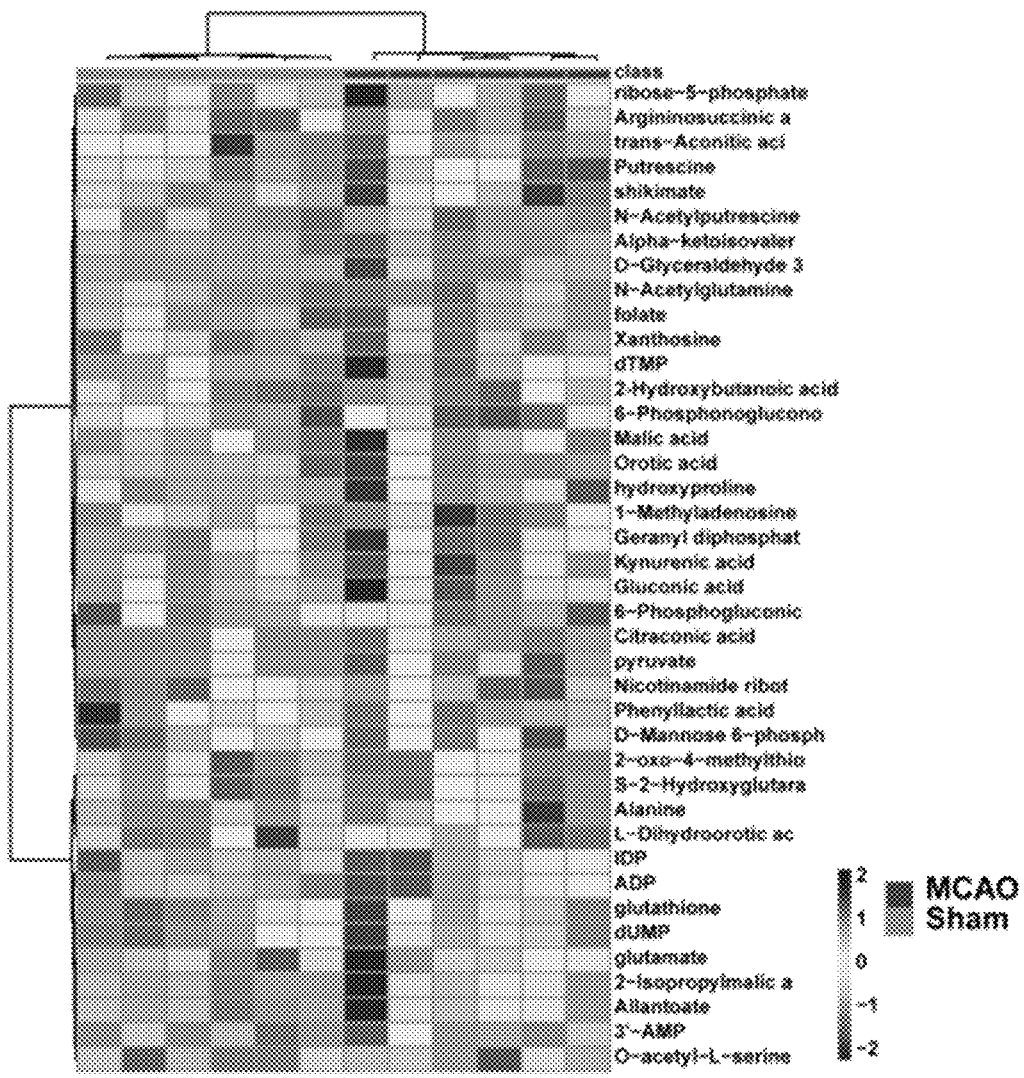
Figure 1D:
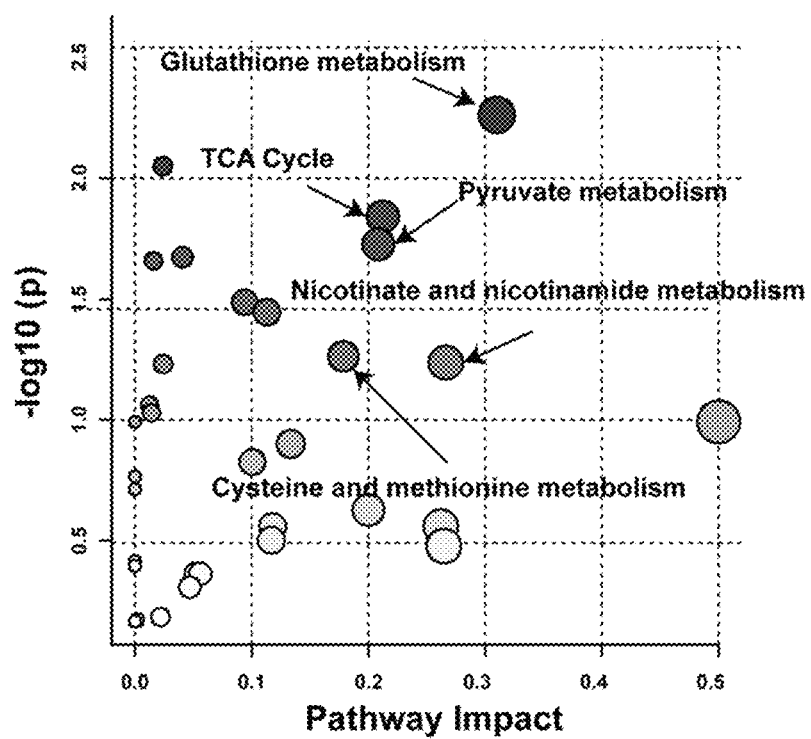

The occurrence of cerebral ischemic stroke was simulated by constructing cell models and rat MCAO models, and changes were studied in metabolite levels in the cerebral cortex of model rats. When cerebral ischemic stroke occured, arterial occlusion led to reduced CBF around the infarct core, deep hypoxia of brain tissue and microvascular dysfunction, triggering an imbalance of metabolic homeostasis. The results show that a model group and a control group have significantly different metabolic characteristics (as shown in FIG. 1A); an energy substrate nicotinamide adenine dinucleotide (NAD) and reducing equivalents glutathione (GSH), oxidized glutathione (GSSG), and NADPH are decreased (as shown in FIG. 1B and FIG. 1C). After enriching differential metabolites, it is found that the TCA pathway, the niacin and niacinamide metabolic pathway, and the GSH pathway have changed significantly (see FIG. 1D). The above paths are key paths to maintain a steady state of energy and reduction equivalent. It shows that the cerebral ischemic stroke causes cerebral metabolic disorders, which are mainly reflected in the influence on energy and redox metabolism.

1.3. Selection and Determination of the Fructose Pathway

Cerebral ischemic stroke triggered an imbalance of metabolic homeostasis. The applicant team started with current and effective endogenous metabolic control methods to find a therapeutic target for the cerebral ischemic stroke. IPC is the strongest endogenous ischemic protection method. Through transient, non-lethal ischemic treatment, an endogenous protection mechanism was activated to make the tissues tolerate a lethal ischemic injury.

Figure 2:
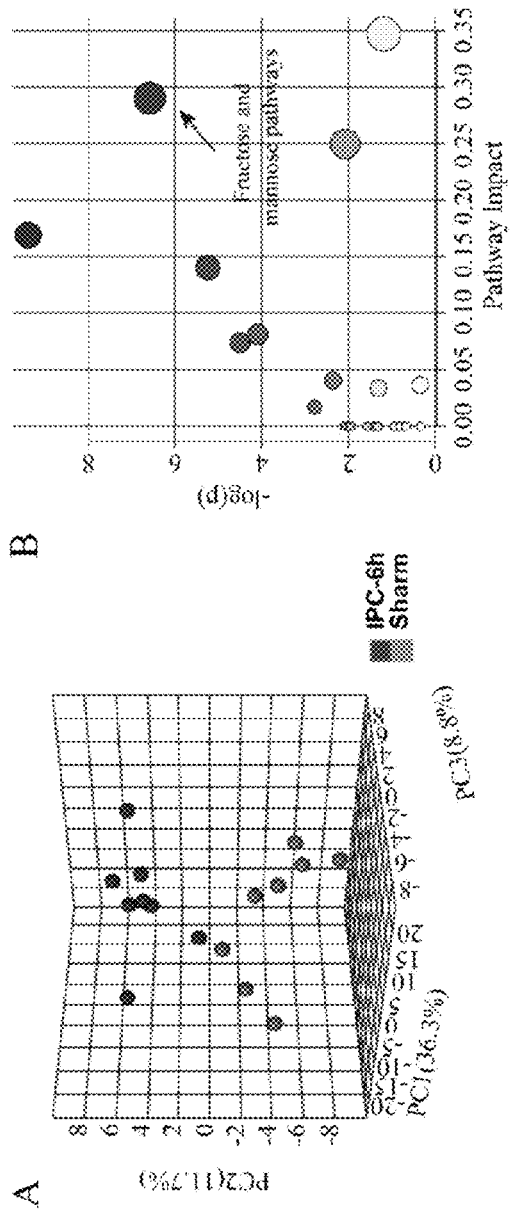
FIG. 2 shows that a fructose pathway is significantly up-regulated in the rat after 6 h of ischemic preconditioning (IPC) treatment.
Figure 3:
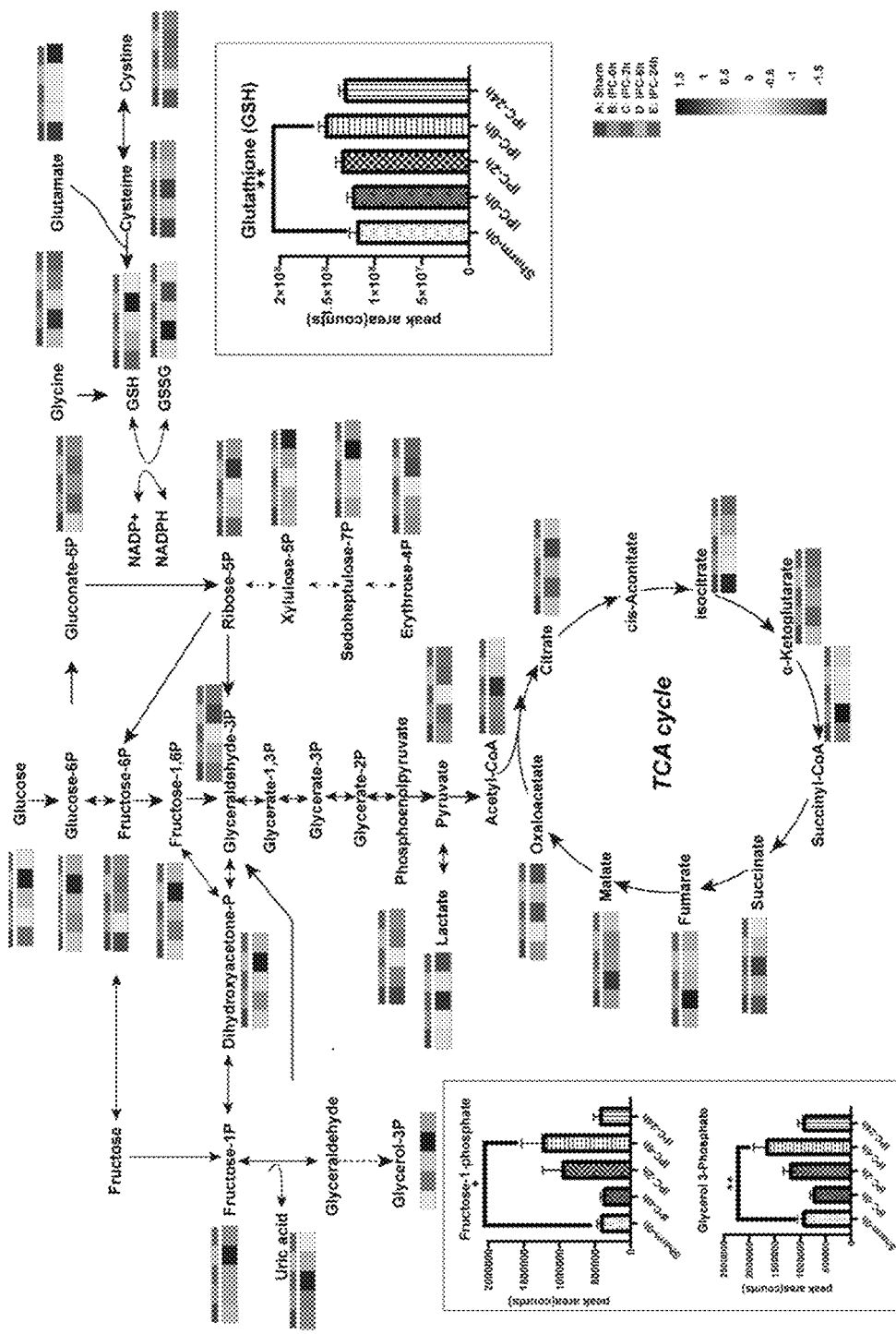
FIG. 3 shows a time-specific regulation profile of a fructose metabolism pathway.
Figure 4A:
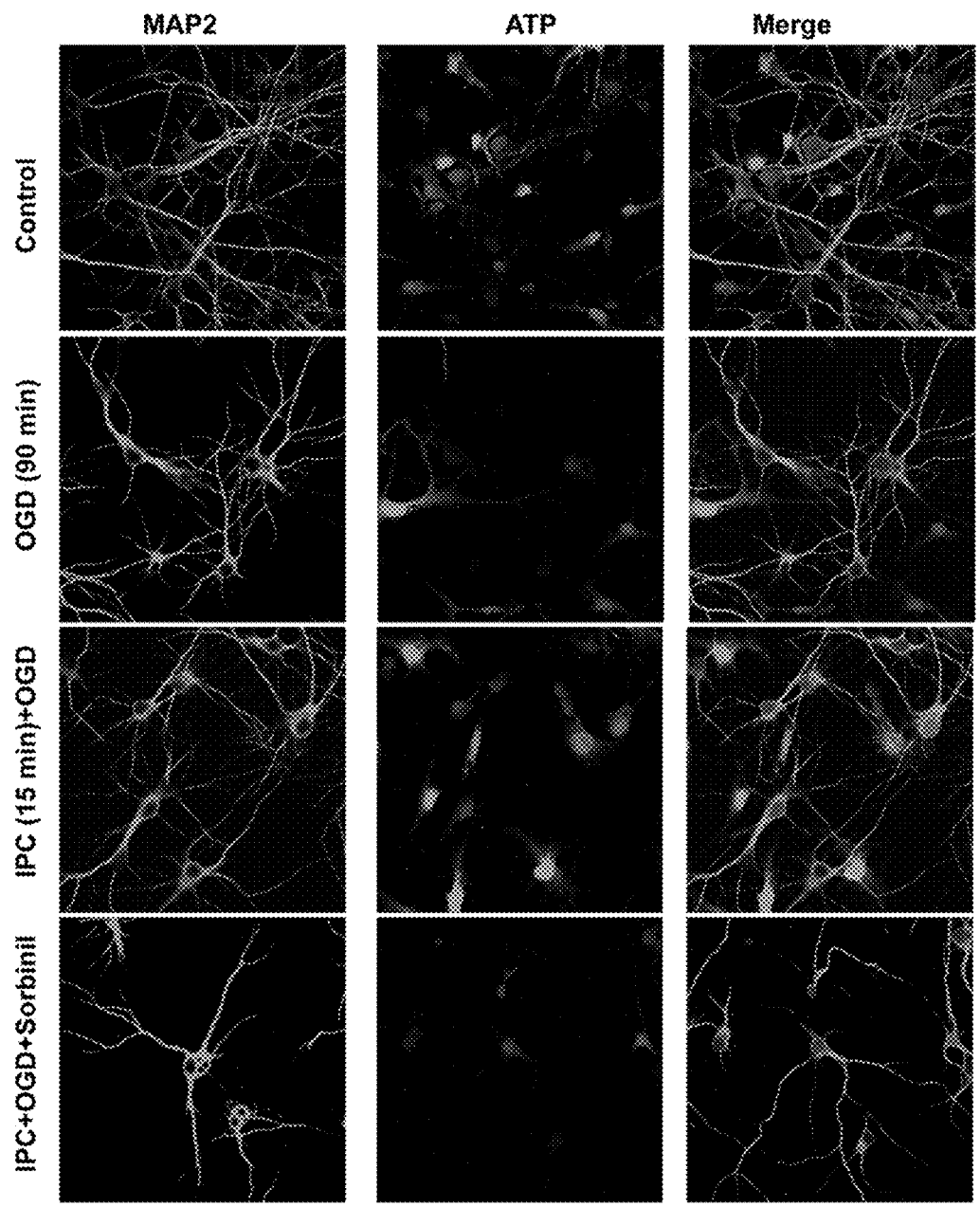
FIGS. 4A-B shows an effect of the fructose pathway on an ATP level of days in vitro 7 (DIV7) neurons.
Figure 4B:
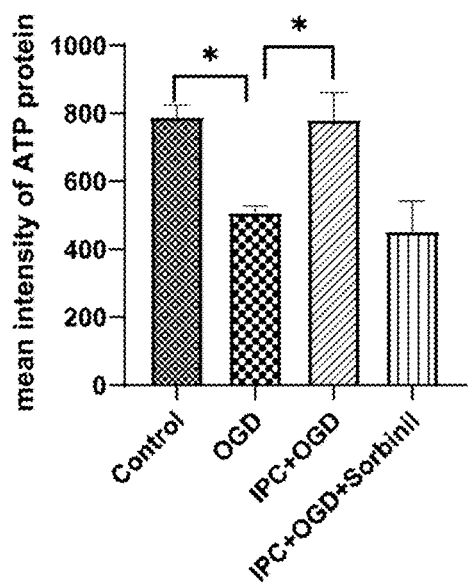
Figure 5A:
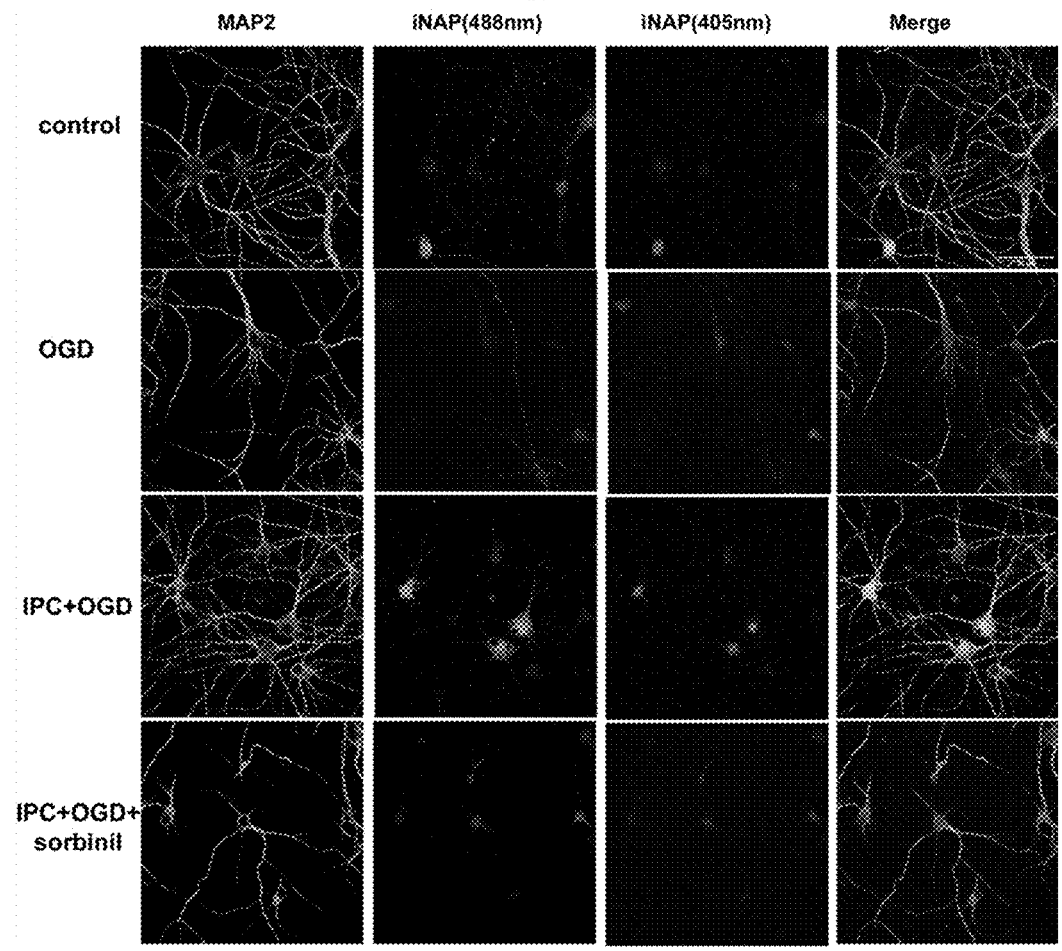
FIGS. 5A-B. shows an effect of the fructose pathway on an NADPH level of the DIV7 neurons.
Figure 5B:
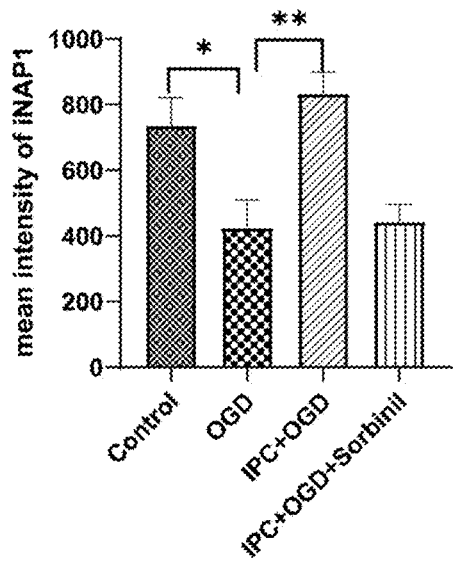

The rats were treated with IPC, and metabolome analysis was conducted on the cerebral cortex at 0, 2, 6 and 24 h after the IPC treatment. It is found that after the IPC treatment, time-specific metabolic changes are triggered in the rat cerebral cortex at the metabolite level (as shown in FIG. 2), which show a time-specificity; after 6 h of the IPC treatment, the glycolytic pathway, the PPP pathway and the fructose pathway were significantly up-regulated, with particularly significant changes. And compared with the control group, there are significant changes in metabolites fructose-1-phosphate (F1P) and glycerol-3-phosphate (G3P) on the fructose pathway (as shown in FIG. 3). It suggests that the fructose pathway is one of the important pathways of ischemic cerebral injury.

Secondly, to further verify effects of the fructose pathway in IPC ischemia protection, a fructose pathway inhibitor sorbinil was added at the cellular level. It is found that after the fructose pathway is inhibited, the IPC no longer increases the contents of ATP and NADPH (as shown in FIGS. 4A-B and FIGS. 5A-B). It suggests that the fructose pathway has a clear role in regulating the ischemic cerebral injury, and can maintain the energy and reduction equivalent homeostasis.

Through target screening, the key component of fructose pathway, fructose, was finally selected to verify effects on the ischemic cerebral injury at the animal and cellular levels.

Example 2 Therapeutic Effect of Fructose on an Ischemic Cerebral Injury 2.1 Evaluation Index of the Ischemic Cerebral Injury (1) Behavioral evaluation: the behavioral evaluation was conducted by Longa scoring method, where a scoring standard was as follows: 0 points=no nerve damage, 1 point=left forelimb extension disorder, 2 points=whirling towards the left, 3 points=falling towards the left while walking, 4 points=unconsciousness, 5 points=death.

(2) Determination of an area of cerebral infarction by TTC staining method: a whole rat brain was dissected and separated, placed in a mold, cerebellum and olfactory bulb were discarded, a coronal brain slice with a thickness of about 2 mm was cut out, and the brain slice was quickly placed in a 2% TTC phosphate buffer solution, and incubation was conducted at 37° C. in the dark for 15-20 min, where the brain slice was turned over every 3-5 min during the incubation; after the incubation, the brain slice was taken out and washed with PBS, and soaked in 4% paraformaldehyde (PFA) overnight; and the brain slice was taken out and washed with PBS, and photographed, and the area of cerebral infarction was calculated by ImageJ. Data statistics was conducted by Graphpad Prism software, means between multiple groups were compared by one-way analysis of variance (One-Way ANOVA), and the means between the groups were compared in pairs.

(3) Survival of neurons: a survival state of neurons was counted by TUNEL staining and immunofluorescence staining; the neuronal cells were subjected to growing on glass coverslips, fixated with 4% PFA for 10 min, washed with PBS, and subjected to incubation in a blocking buffer for 1 h, and a MAP2 primary antibody working solution was added to conduct culture overnight at 4° C.; the cells were washed with PBS, a MAP2 secondary antibody working solution was added to incubate at room temperature for 1 h; the cells were washed with PBS, subjected to TUNEL staining, and a mounting agent containing 4',6-diamidino-2-phenylindole (DAPI) was added for mounting. Data was collected through a focusing microscope and the number of cell deaths was counted using ImageJ.

(4) Content of ATP and NADPH: cortical neurons were isolated from P0-P1 suckling mice, the neurons were inoculated on a 7th day by adding a lentiviral transfection protein vector that specifically detects ATP and a lentiviral transfection protein vector iNap that specifically detects NADPH; the neurons were fixated with 4% PFA, subjected to immunofluorescence staining, and data was collected through a confocal microscope, the fluorescence intensity of virus vector protein was counted using ImageJ, and the contents of ATP and NADPH were calculated.

2.2. Effect of Fructose Administration at Different Stages on OGD-Injured Neurons By detecting an expression level of the lentiviral transfection protein vector that specifically detects ATP and the lentiviral transfection protein vector iNap that specifically detects NADPH in the primary neuron culture system, the levels are characterized for neuronal energy metabolism and redox metabolism.

(1) Neuron survival: DIV7 neurons were divided into four groups: a control group, an OGD group (for OGD treatment), an OGD+Fru(per) group (fructose treatment during OGD treatment), and an OGD+Fru(post) group (fructose treatment in a reperfusion stage after OGD treatment). The neurons was subjected to reperfusion for 24 h after the end of OGD, fixated with 4% PFA for 10 min, washed with PBS, and a MAP2 primary antibody working solution was added; the cells were washed with PBS, a MAP2 secondary antibody working solution was added; the cells were washed with PBS, subjected to TUNEL staining, and a mounting agent containing DAPI was added for mounting. The survival of neurons was observed.

Figure 6A:
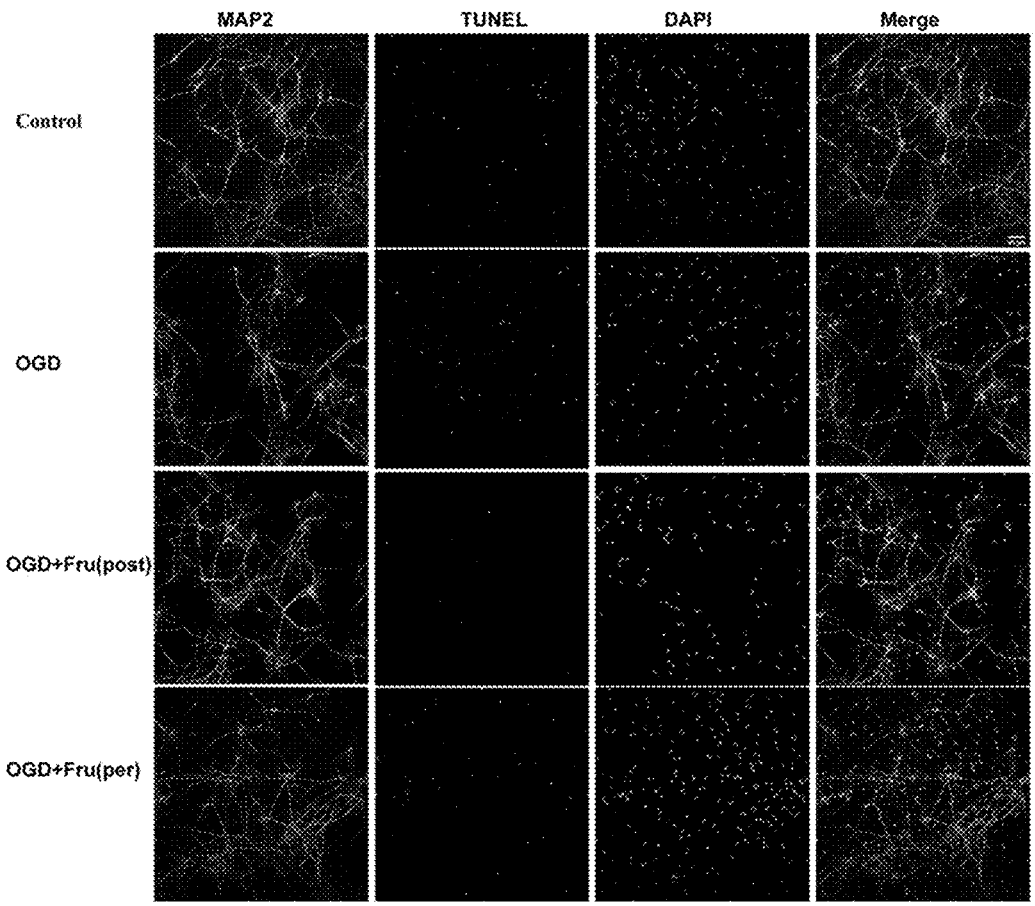
FIGS. 6A-C shows an effect of fructose administration at different stages on a survival rate of OGD-injured neurons.
Figure 6B:
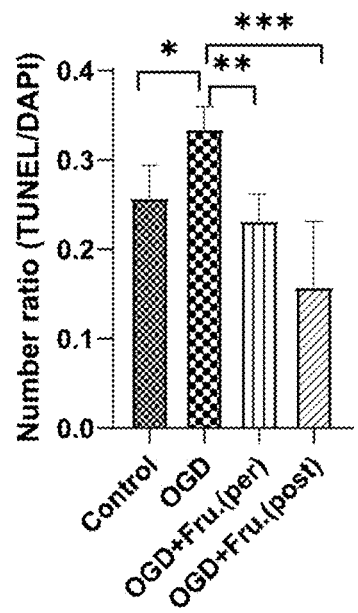
Figure 6C:
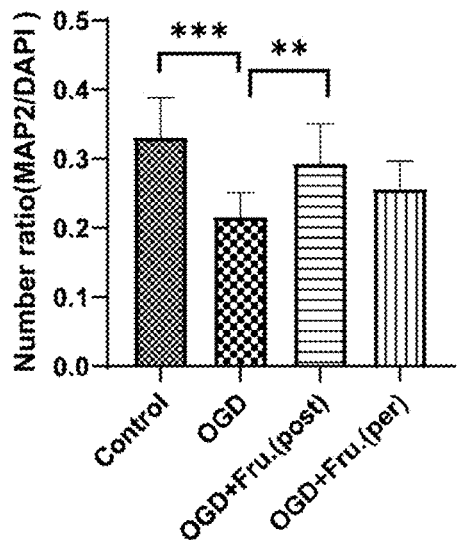
Figure 7A:
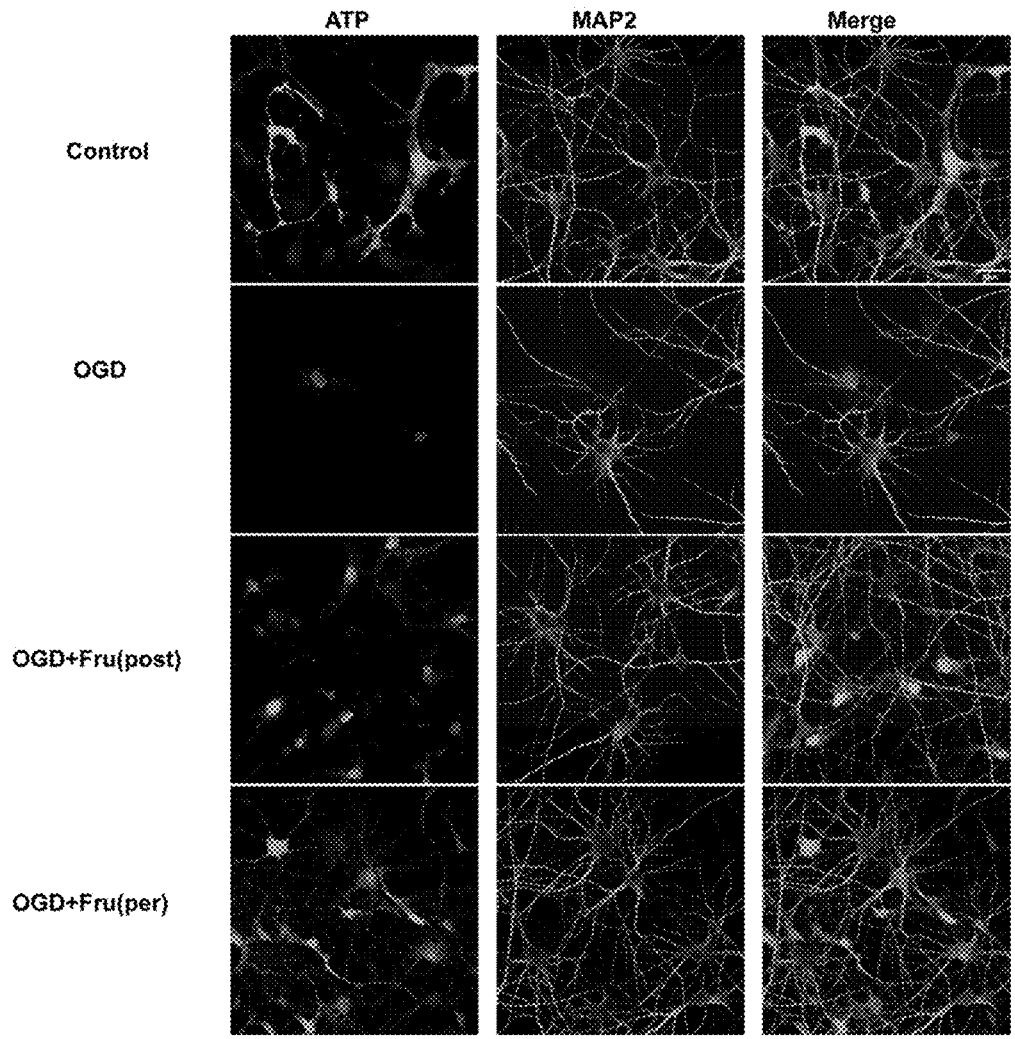
FIGS. 7A-B shows an effect of the fructose administration at different stages on an ATP production of the OGD-injured neurons.
Figure 7B:
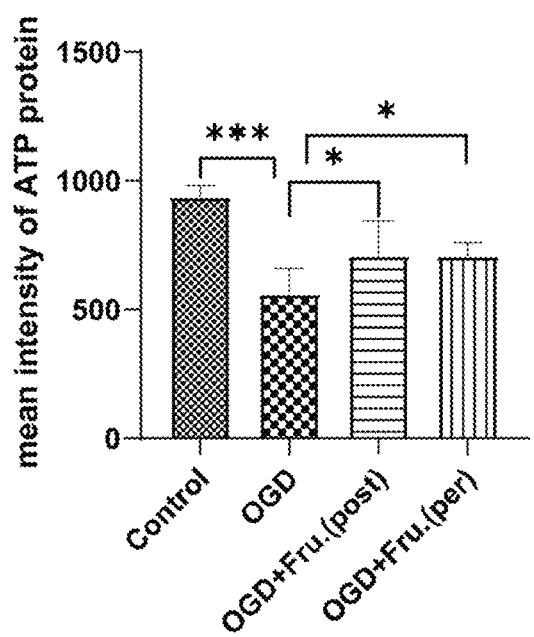
Figure 8A:
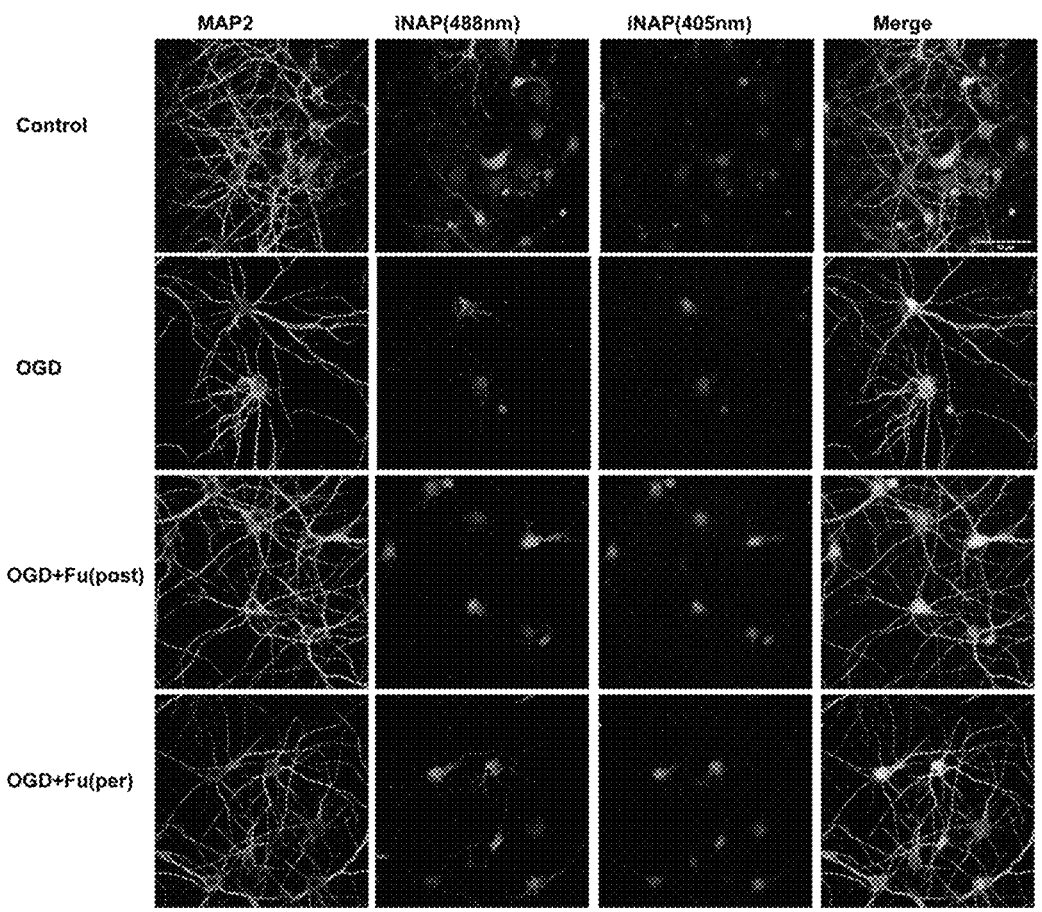
FIGS. 8A-B shows an effect of the fructose administration at different stages on an NADPH production of the OGD-injured neurons.
Figure 8B:
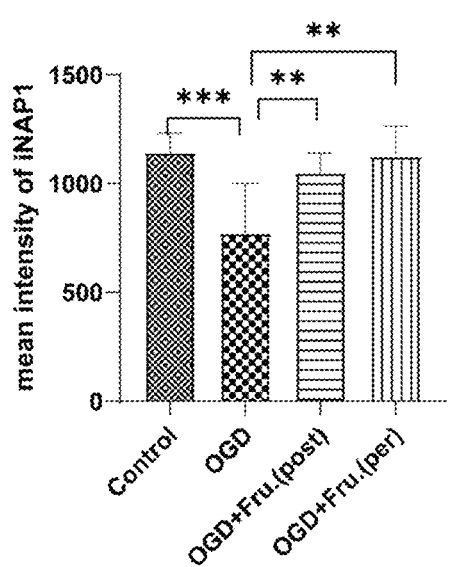
Figure 9A:
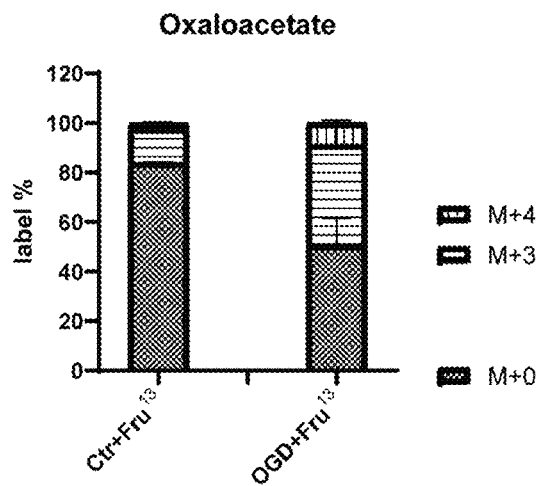
FIGS. 9A-E shows distribution of isotope-labeled fructose in a pentose phosphate pathway (PPP) and a tricarboxylic acid (TCA) cycle pathway under normal conditions and OGD treatment.
Figure 9B:
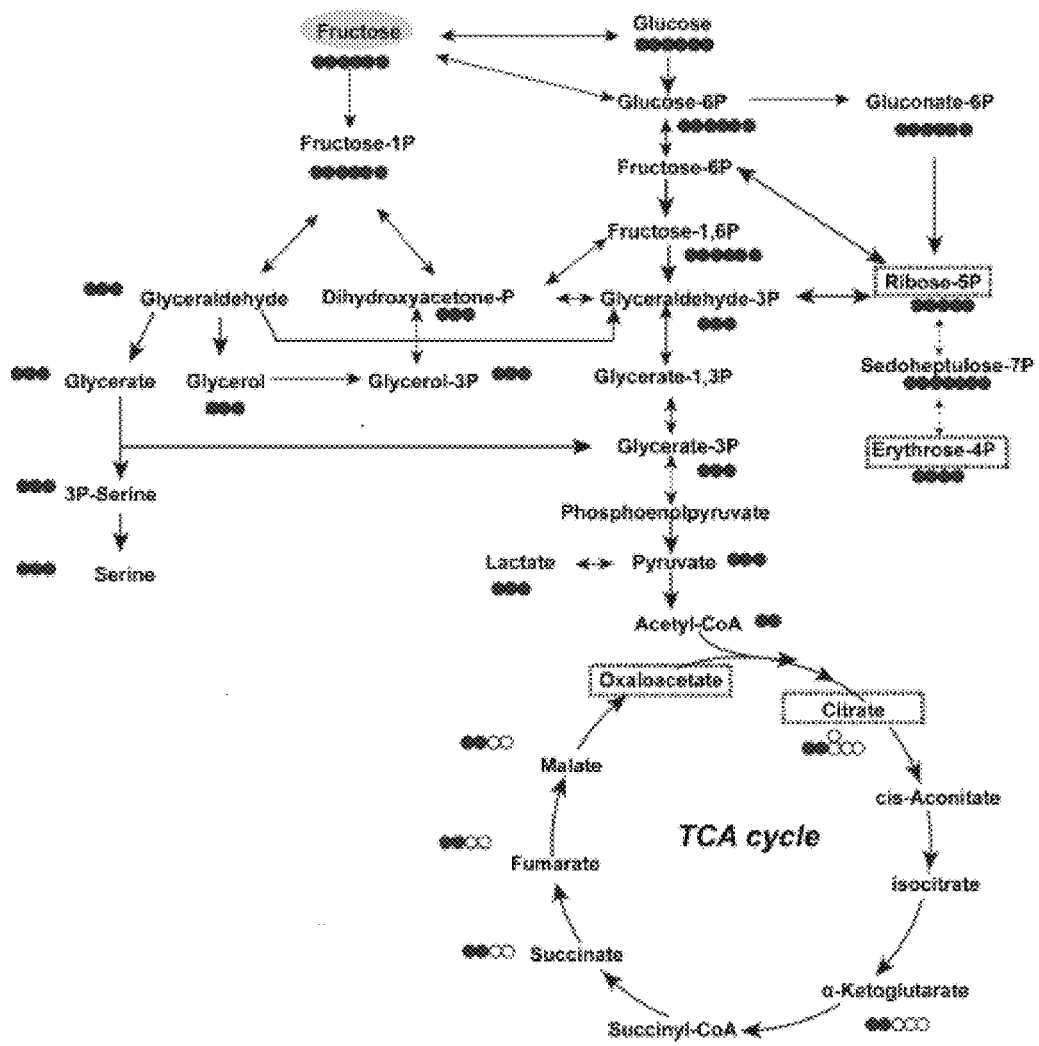
Figure 9C:
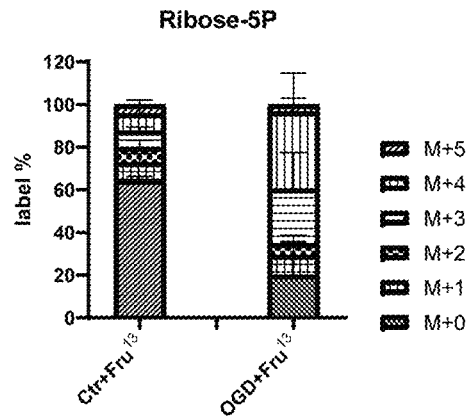
Figure 9D:
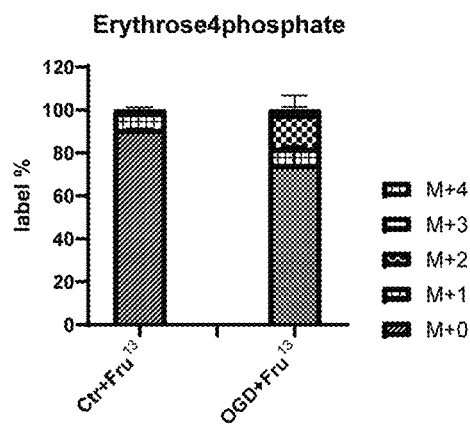
Figure 9E:
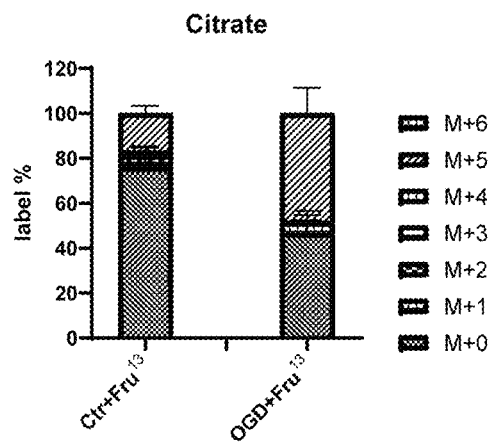

The results show that adding fructose in both the OGD phase and the reperfusion phase can reduce the neuronal death rate caused by OGD, as shown in FIGS. 6A-C.

(2) Content of ATP and NADPH: cortical neurons were isolated from P0-P1 suckling mice, the neurons were inoculated on a 7th day by adding a lentiviral transfection protein vector that specifically detects ATP and a lentiviral transfection protein vector iNap that specifically detects NADPH; the neurons were divided into four groups: a control group, an OGD group (for OGD treatment), an OGD+Fru(per) group (fructose treatment during OGD treatment), and an OGD+Fru(post) group (fructose treatment in a reperfusion stage after OGD treatment). Reperfusion was conducted 24 h after OGD; the neurons were fixated with 4% PFA, subjected to MAP2 immunofluorescence staining to observe the content of ATP and NADPH of the neurons.

The results show that adding fructose in both the OGD phase and the reperfusion phase can enhance the decrease in ATP and NADPH production of neurons caused by OGD; that is, the fructose can enhance energy metabolism and redox metabolism of neurons, as shown in FIGS. 7A-B and FIGS. 8A-B.

(3) Increase of Influx of PPP and TCA Pathways by the Fructose

A metabolic flux experiment was conducted, U-13C-fructose was added to DIV7 neurons, and distribution of the fructose in each metabolic pathway was observed under normal conditions and after OGD treatment. It is found that after OGD treatment, compared with the control group, a 13C labeling rate increases in the key metabolites of the PPP pathway, ribose-5-phosphate and erythrose-4 phosphate. It shows that when OGD occurs, the distribution of fructose to the PPP pathway is enhanced, that is, the level of cell NADPH is increased by strengthening the influx to PPP, thereby maintaining the redox balance. Meanwhile, after the OGD treatment, compared with the control group, a 13C labeling rate increases in oxaloacetic acid and citric acid, the key metabolites of the TCA pathway. The results show that the influx of fructose into TCA is enhanced when OGD occurs, that is, the cell energy supply is maintained by enhancing the TCA, as shown in FIGS. 9A-E.

2.3. Effect after Fructose Administration by Different Routes on MCAO Rats 250-300 g male SD rats were divided into three groups, and subjected to MCAO modeling (MCAO group), MCAO modeling combined with tail vein injection of fructose after suture plug removal (MCAO+Fru-1 group), and MCAO modeling combined with intraperitoneal injection of fructose after suture plug removal (MCAO+Fru-2 group), respectively. The modeling was specifically as follows: the rats were anesthetized with isopentane, the skin was cut off to expose the common carotid artery, internal carotid artery, and external carotid artery at right side, a silicone suture plug was inserted through the external carotid artery to a beginning of the middle cerebral artery, the suture plug was removed after 1.5 h, and fructose administration was conducted immediately follow the above treatment plans; after 24 h of administration, behavioral evaluation was conducted by *Longa* scoring method; the rats were sacrificed by anesthesia, and brains were taken out to observe an area of cerebral infarction after TTC staining.

Figure 10A:
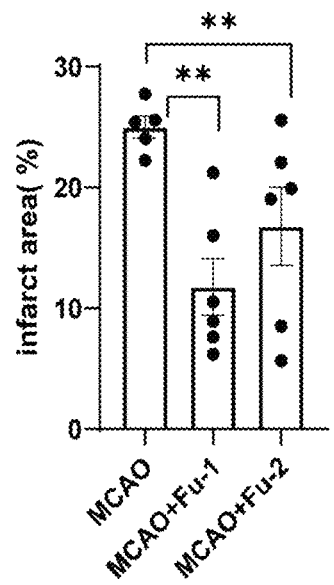
FIGS. 10A-C shows effects of fructose treated by different routes of administration on neurobehavior and cerebral infarction in an MCAO rat.
Figure 10B:
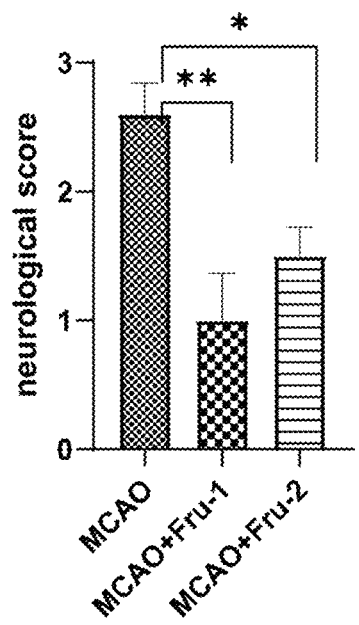
Figure 10:
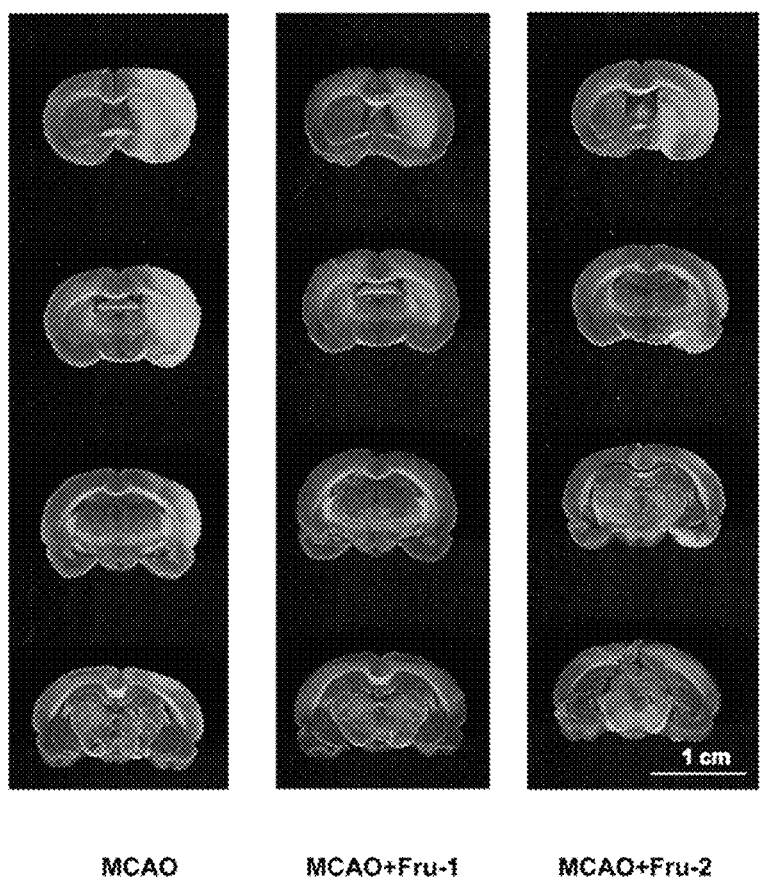

The results show that the administration of fructose in both ways can improve the neurobehavioral characteristics of MCAO rats and reduce the area of cerebral infarction. The tail vein injection is generally better than the intraperitoneal injection, as shown in FIGS. 10A-C.

In summary, various experimental data show that the fructose has a significant therapeutic effect on OGD neurons and MCAO rats, which is expected to be developed as a novel drug for treating ischemic cerebrovascular diseases, especially for cerebral ischemic stroke.

2.4. Effect of Different Concentrations Fructose on Cell Viability

Figure 11:
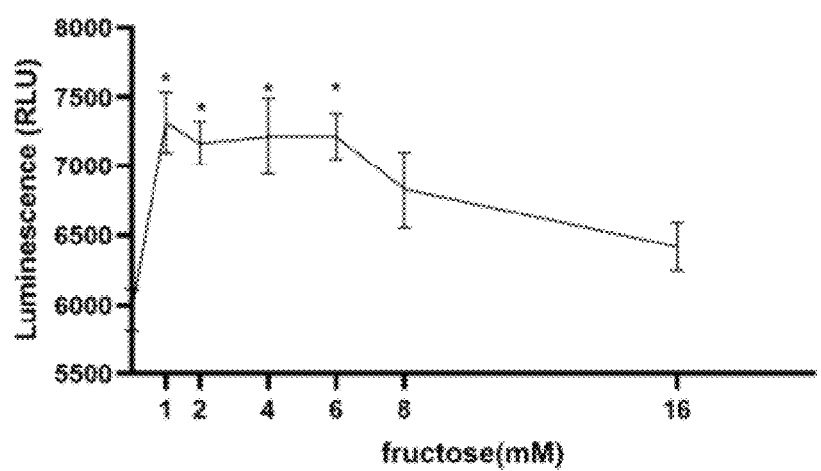
FIG. 11 shows an effect of different concentrations of fructose on cell viability.

Effects of different concentrations of fructose on the viability of DIV7 neurons were studied using a CellTiter-Glo® Luminescent cell viability test kit, and an added concentration of the fructose was explored in the cell system. The results show that the fructose has a better effect of improving the activity of DIV7 neuronal cells at 1-6 mM, as shown in FIG. 11.

Example 3: Comparison of Effects of Fructose, Fructose-1,6-Bisphosphate and Glycerol Fructose in Prevention and Treatment of Ischemic Injury The existing fructose-related drugs in the prior art were selected as follows: fructose-1,6-bisphosphate (F1, 6P) and glycerol fructose (G. Fru.), and therapeutic effects of the two were verified on ischemic injury through comparative experiments.

3.1. Effects of Fructose, Fructose-1,6-Bisphosphate and Glycerol Fructose on a Viability of the DIV7 Neurons Effects of different concentrations (0, 1, 2, 4, 6, 8 and 16 mM) of the fructose (Fru.), the fructose-1,6-bisphosphate (F1,6P) and the glycerol fructose (G.Fru.) on the viability of DIV7 neurons were studied using a CellTiter-Glo® Luminescent cell viability test kit.

Figure 12:
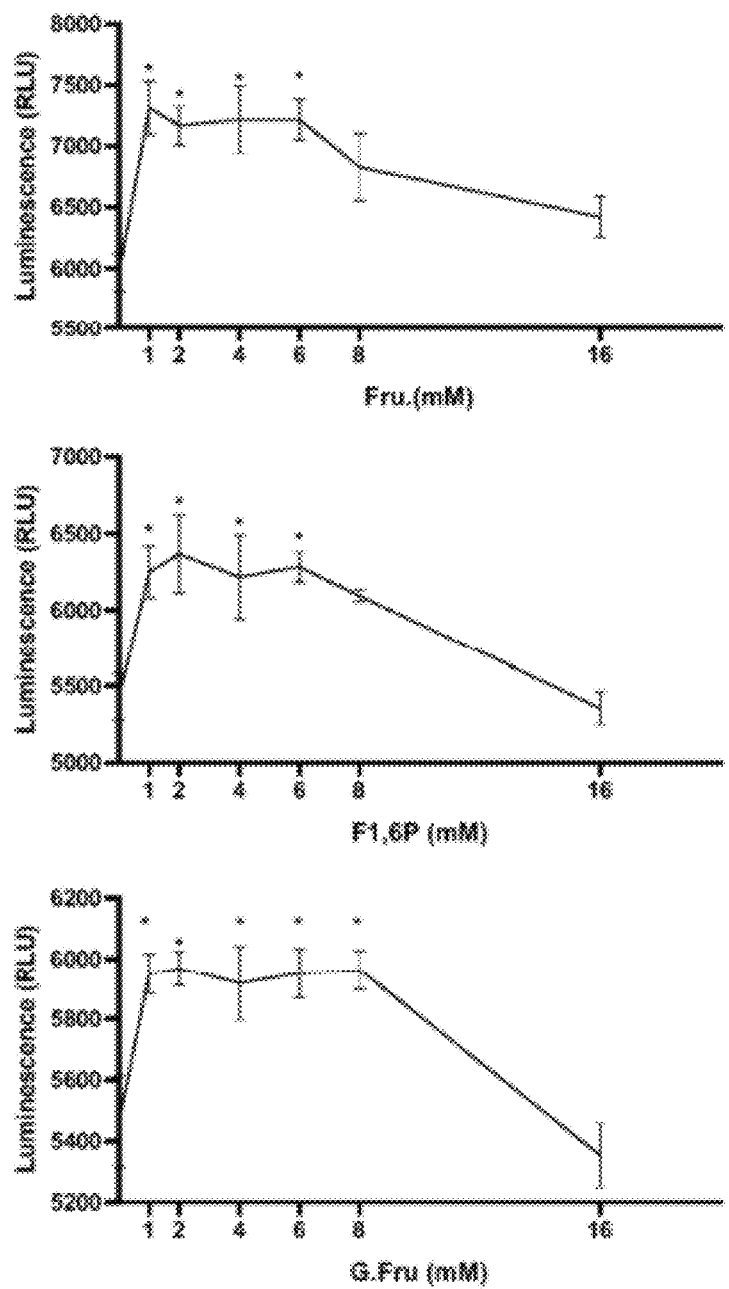
FIG. 12 shows effects of fructose, fructose-1,6-bisphosphate and glycerol fructose on a viability of the DIV7 neurons, and results show that the fructose can significantly enhance viability of the neurons.

The results show that the three components can improve neuron viability, where the fructose has an improvement effect on neuron viability significantly better than that of the fructose-1,6-bisphosphate and the glycerol fructose, as shown in FIG. 12 (each concentration group is compared with the 0 mM group, and * $P<0.05$).

3.2. Effects of the Fructose, the Fructose-1,6-Bisphosphate and the Glycerol Fructose in Protecting OGD-Injured Neurons The CellTiter-Glo® Luminescent cell viability test kit was used: the neuronal cells were cultured using a 96-well plate, and OGD treatment was conducted on neurons for 1.5 h on a 7th day; fructose, fructose-1,6-bisphosphate and glycerol fructose were added each at a concentration of 2 mM; after 24 h, the cell viability was detected by the kit.

Figure 13:
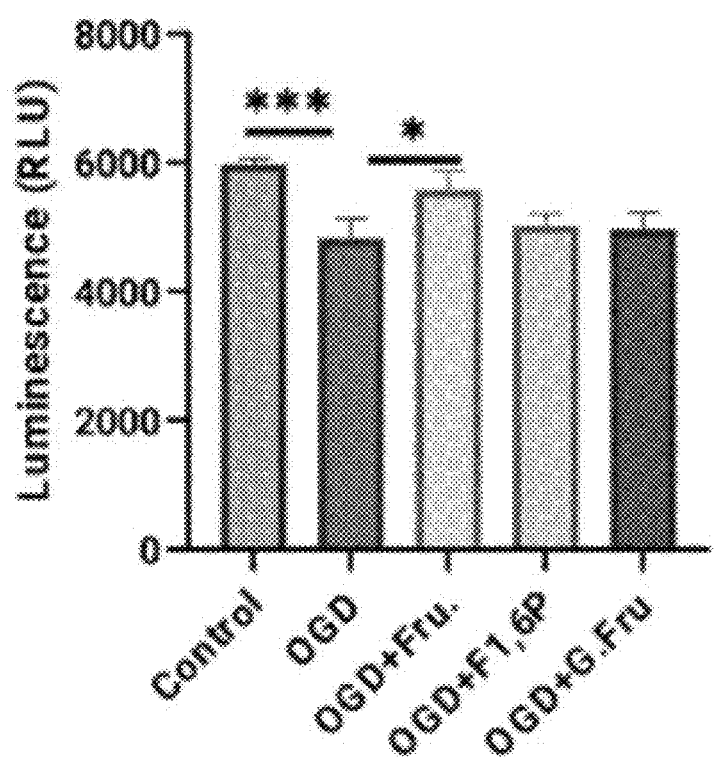
FIG. 13 shows effects of fructose, fructose-1,6-bisphosphate and glycerol fructose on a viability of the OGD-injured neurons.

The results show that OGD significantly reduced cell viability; the fructose can significantly increase the cell viability of OGD-injured neurons; however, in this model system, the fructose-1,6-bisphosphate and the glycerol fructose have a tendency to increase the viability of OGD-injured neurons, but show significant differences, as shown in FIG. 13 (* $P<0.05$, *** $P<0.001$).

Immunofluorescence staining method: the neurons were cultured for 7 d, and subjected to OGD treatment for 1.5 h; fructose, fructose-1,6-bisphosphate and glycerol fructose were added each at a concentration of 2 mM; after 24 h, MAP2 and DAPI staining were conducted.

Figure 14:
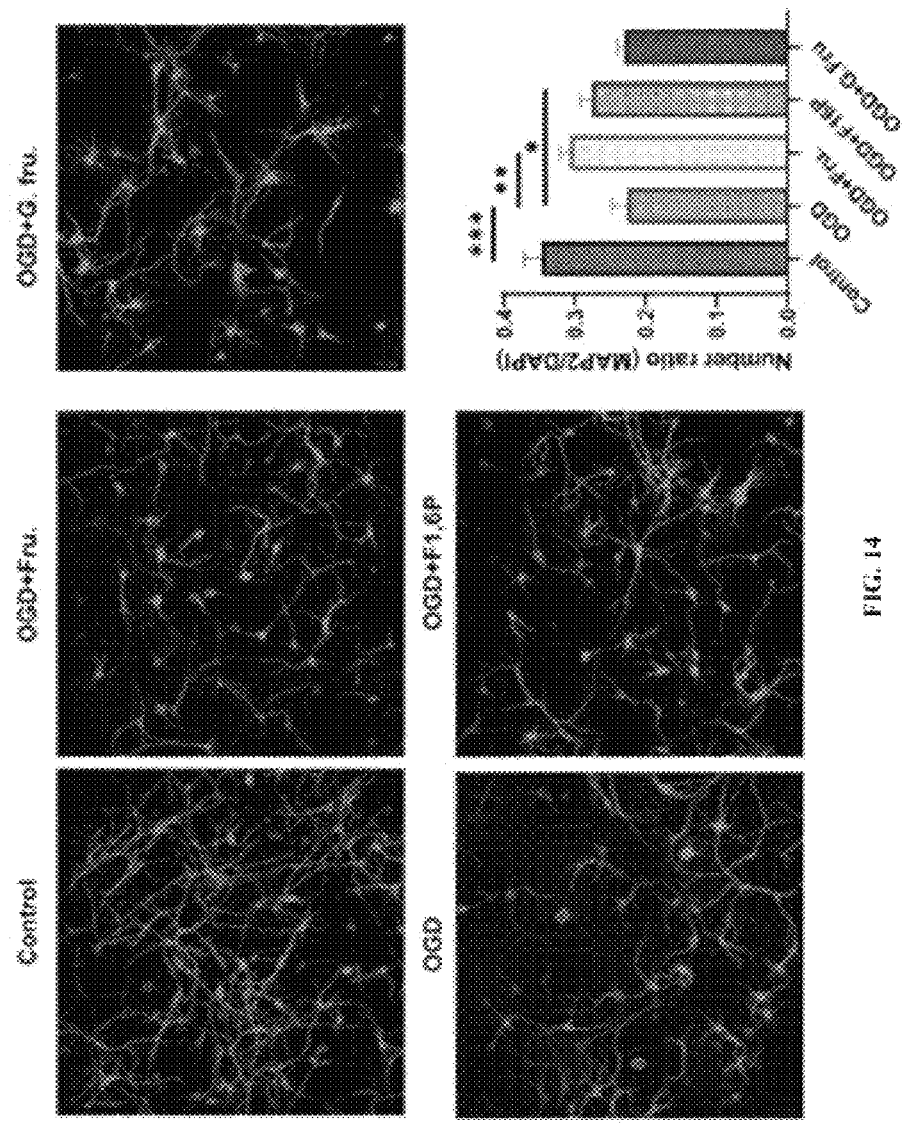
FIG. 14 shows effects of fructose, fructose-1,6-bisphosphate and glycerol fructose on the survival rate of DIV7 neurons.

The results show that OGD significantly reduces the survival rate of neurons; after drug treatment, the glycerol fructose has a slight effect on the survival rate of neurons, and the fructose and the fructose-1,6-bisphosphate each can improve the survival rate of the neurons, where the fructose has a significantly better effect than the fructose-1,6-bisphosphate. The results are as shown in FIG. 14 (* $P<0.05$,  $P<0.01$, * $P<0.001$).

What is claimed is:

1. A method of treating an ischemic cerebral injury, the method comprising administrating a drug comprising fructose to a subject having an ischemic cerebral injury, wherein the fructose is the only active ingredient.

2. The method according to claim 1, wherein the ischemic cerebral injury is a cerebral ischemic stroke.

3. The method according to claim 2, wherein the active ingredient provides the following cerebral protection effects upon administering the drug to the subject: regulating energy metabolism and redox metabolism, improving a survival rate of ischemic-injured neurons, reducing an area of cerebral infarction caused by the cerebral ischemic stroke, and improving neurobehavioral characteristics of the cerebral ischemic stroke.

4. The method according to claim 1, wherein the step of administering the drug comprises an administration selected from the group consisting of intravenous injection, intramuscular injection, intraperitoneal injection, oral administration, nasal drip administration, sublingual administration, intracranial injection, interventional administration, implantable drug administration, and application and smearing administration.

5. The method according to claim 2, wherein the step of administering the drug comprises an administration selected from the group consisting of intravenous injection, intramuscular injection, intraperitoneal injection, oral administration, nasal drip administration, sublingual administration, intracranial injection, interventional administration, implantable drug administration, and application and smearing administration.

6. The method according to claim 3, wherein the step of administering the drug comprises an administration selected from the group consisting of intravenous injection, intramuscular injection, intraperitoneal injection, oral administration, nasal drip administration, sublingual administration, intracranial injection, interventional administration, implantable drug administration, and application and smearing administration.

7. The method according to claim 1, wherein the drug has a dosage form comprising an injection, a patch, a drop, a granule, a tablet, an effervescent tablet, a pill, a liniment, a drop pill, a sublingual tablet, a microneedle patch and a cream.

8. The method according to claim 2, wherein the drug has a dosage form comprising an injection, a patch, a drop, a granule, a tablet, an effervescent tablet, a pill, a liniment, a drop pill, a sublingual tablet, a microneedle patch and a cream.

9. The method according to claim 3, wherein the drug has a dosage form comprising an injection, a patch, a drop, a granule, a tablet, an effervescent tablet, a pill, a liniment, a drop pill, a sublingual tablet, a microneedle patch and a cream.

10. The method according to claim 1, wherein the drug further comprises a pharmaceutically acceptable adjuvant.

11. The method according to claim 2, wherein the drug further comprises a pharmaceutically acceptable adjuvant.

12. The method according to claim 3, wherein the drug further comprises a pharmaceutically acceptable adjuvant.

13. The method according to claim 1, wherein the drug is suitable for administration at a cerebral infarction stage, a surgery or drug treatment stage, a stroke rehabilitation stage, a stage before thrombectomy, a stage after thrombectomy, a stage before thrombolysis, and a stage after thrombolysis.

14. The method according to claim 2, wherein the drug is suitable for administration at a cerebral infarction stage, a surgery or drug treatment stage, a stroke rehabilitation stage, a stage before thrombectomy, a stage after thrombectomy, a stage before thrombolysis, and a stage after thrombolysis.

15. The method according to claim 3, wherein the drug is suitable for administration at a cerebral infarction stage, a surgery or drug treatment stage, a stroke rehabilitation stage, a stage before thrombectomy, a stage after thrombectomy, a stage before thrombolysis, and a stage after thrombolysis.

16. The method according to claim 4, wherein the drug is suitable for administration at a cerebral infarction stage, a surgery or drug treatment stage, a stroke rehabilitation stage, a stage before thrombectomy, a stage after thrombectomy, a stage before thrombolysis, and a stage after thrombolysis.

17. The method according to claim 1, wherein the active ingredient provides the following cerebral protection effects upon administering the drug to the subject: regulating energy metabolism and redox metabolism, improving a survival rate of ischemic-injured neurons, reducing an area of cerebral infarction caused by the cerebral ischemic stroke, and improving neurobehavioral characteristics of the cerebral ischemic stroke.

18. The method according to claim 17, wherein the step of administering the drug comprises an administration selected from the group consisting of intravenous injection, intramuscular injection, intraperitoneal injection, oral administration, nasal drip administration, sublingual administration, intracranial injection, interventional administration, implantable drug administration, and application and smearing administration.

* * * * *